United States Patent
Lin et al.

(10) Patent No.: US 7,214,838 B2
(45) Date of Patent: May 8, 2007

(54) METHOD FOR TRANSFERRING TCPX INTO TFPX

(75) Inventors: Chun-Hsu Lin, Taipei (TW); Jao-Jou Tu, Guansi Township, Hsinchu County (TW); Te-Po Liou, Longtan Township, Taoyuan County (TW); Shieh-Jun Wang, Taipei (TW)

(73) Assignee: Yuan-Shin Materials Technology Corp., Taipei (TW)

( * ) Notice: Subject to any disclaimer, the term of this patent is extended or adjusted under 35 U.S.C. 154(b) by 156 days.

(21) Appl. No.: 11/189,709

(22) Filed: Jul. 27, 2005

(65) Prior Publication Data

US 2006/0211894 A1    Sep. 21, 2006

(30) Foreign Application Priority Data

Mar. 21, 2005   (TW)   ............................... 94108583 A

(51) Int. Cl.
 *C07C 22/08* (2006.01)
(52) U.S. Cl. .................. 570/145; 570/123; 570/143; 570/144
(58) Field of Classification Search ................ 570/145, 570/143, 123, 144
See application file for complete search history.

(56) References Cited

U.S. PATENT DOCUMENTS

| | | | |
|---|---|---|---|
| 3,878,246 | A | 4/1975 | Mathey et al. |
| 5,210,341 | A | 5/1993 | Dolbier, Jr. et al. |
| 5,536,892 | A | 7/1996 | Dolbier, Jr. et al. |
| 5,841,005 | A | 11/1998 | Dolbier, Jr. et al. |
| 5,849,962 | A | 12/1998 | Dolbier, Jr. et al. |
| 6,043,397 | A | 3/2000 | Teshima et al. |
| 6,150,499 | A | 11/2000 | Dolbier, Jr. et al. |
| 6,222,064 | B1 | 4/2001 | Lal et al. |
| 6,284,933 | B1 * | 9/2001 | Dolbier et al. ............... 570/145 |

FOREIGN PATENT DOCUMENTS

EP    0930287    7/1999
WO    WO 98/24743    6/1998

OTHER PUBLICATIONS

S. A. Fuqua et. al.; *Synthesis And Chemistry Of Several Fluorinated p-Xylenes Designed As Precursors For α, α, α', α'-Tetraluoro-p-Xylylene;* 1964; Tetrahedron, vol. 20, pp. 1625-1632.
Leslie Dolby-Glover; *Fluoroorganic compounds in industry: applications and synthesis;* Aug. 4, 1986; Chemistry and Industry, pp. 518-523.
James H. Clark et. al.; *The Synthesis of Organofluorine Compounds Using Potassium Fluoride-Tetraphenylphosphonium Bromide Systems;* 1987; Tetrahedron Letter, Bol. 28, No. 1, pp. 111-114.
Yasuo Yoshida et. al.; *A Convenient Synthesis of Fluorobenzaldehydes by $KF/PH_4PBr$/18-Crown-6 Reagent System;* 1988, Chemistry Letters, pp. 1355-1358.
Naoto Yazawa et. al.; *Tetraphenylphosphonium Bromide Catalyzed Flurodenitrations and Fluorodesulfonylations. Efficient Syntheses of m-Fluoroaromatic Compounds;* 1989; Chemistry Letters; pp. 2213-2216.
R. Eric Banks; *'Halex' Fluorination of Chlorinated Benzaldehydes And Benzoyl Chlorides;* 1990; Journal of Fluorine Chemistry, pp. 529-537.
Pinaki S. Bhadury et. al.; *A facile synthesis of organofluorine compounds using a semi-molten mixture tetrabutylammonium bromine and an alkali metal fluoride;* 1995; Journal of Fluorine Chemistry, pp. 185-187.
Yoel Sasson et. al.; *Tetramethylammonium chloride as a selective and robust phase transfer catalyst in a solid-liquid halex reaction: the role of water;* 1996; Chem. Commun., pp. 297-298.
William R. Dolbier, Jr. et. al.; *A New and Practical Synthesis of Octafluoro[2.2]paracyclophane;* 1997, J. Org. Chem, pp. 7500-7502.

* cited by examiner

*Primary Examiner*—Elvis O. Price
(74) *Attorney, Agent, or Firm*—Bacon & Thomas, PLLC

(57) ABSTRACT

A method for transferring TCPX (α, α, α', α'-tetrachloro-p-xylene) into TFPX (α, α, α', α'-tetrafluoro-p-xylene) is disclosed, which comprises the following steps: (a) providing a first reactant comprising TFPX; (b) mixing the first reactant with alkali metal fluorides, TCPX and phase transfer catalyst(s) to form a mixture, wherein the alkali metal fluorides is KF, CsF, NaF, LiF or the combination thereof, the phase transfer catalyst(s) is quaternary ammonium salt, quaternary phosphonium salt or the combination thereof; and (c) heating the mixture.

15 Claims, No Drawings

METHOD FOR TRANSFERRING TCPX INTO TFPX

BACKGROUND OF THE INVENTION

1. Field of the Invention

The present invention relates to a transferring method and, more particularly, to a method for transferring tetrachloro-p-xylene (TCPX) into tetrafluoro-p-xylene (TFPX).

2. Description of Related Art

Because parylene polymer possess numerous advantages for manufacturing purposes, for example, maintaining the coating environment at room temperature, no residual stress after coating and allowing precise controls on the thickness of the deposition film, additionally with parylene polymer film's uniformity, excellent acid resistance and alkali resistance, high transparency and low dielectric constant, it has been widely employed in the practice of electric insulation on printing electric circuit boards, damp-proofing on sensors or medical equipment, anti-corrosion on metal-coating, etc. Presently the highly expected fluoro parylene polymer, for its low dielectric constant and high melting point, will be utilized on dielectric coating in the electrical and coating industries.

Fluoro parylene polymer has the structure (1) as follows:

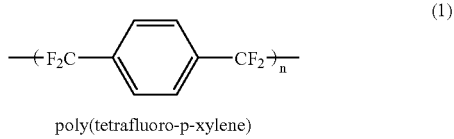

poly(tetrafluoro-p-xylene)

(1)

Fluoro parylene polymer generally is coated on products by means of chemical vapor deposition in a vacuum at room temperature. Products coated with parylene polymer possess not only excellent anticorrosive, damp-proofing and insulating characteristics, but also have the advantages of extra-thin, transparent and poreless properties. Parylene polymer coating is to polymerize the more active monomer on the surface of the object. Unlike the general steps of liquid coating process, this coating process is to have the parylene dimer vaporized first, and as the dimer bonds are cleaved to yield monomer radical at a pyrolysis condition, the monomer radical is polymerized to form parylene polymer.

Moreover, fluoro parylene polymer's dielectric constant decreases as the number of fluorine atoms increases within the polymer, thus octafluoro-2,2-paracyclophane, which is generally used nowadays has the following structure (2):

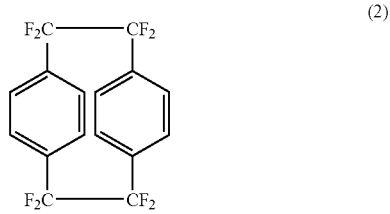

(2)

TFPX ($\alpha$, $\alpha$, $\alpha'$, $\alpha'$-tetrafluoro-p-xylene), as the molecular structure below shows, is a critical precursor after bromization in the process of synthesis for the above dimer.

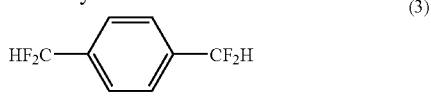

(3)

However, the TFPX synthesis method nowadays is relatively costly, time-consuming and unable to be mass-utilized. For example, although TFPX can be obtained from the preparation by mixing TCPX ($\alpha$, $\alpha$, $\alpha'$, $\alpha'$-tetrachloro-p-xylene) with KF at a proper ratio in either an open or closed reaction container, reacting continuously for 12 hours at a temperature of 260° C.~280° C., a lack of solutions in the reaction will cause a serious gelation problem, similar to what would happen in a solid-state reaction. Such a problem would not only hinder the yield of the desired product, it yet further affects the possibility of production expansion. Other typical synthesis methods involve organic compounds comprising carbonyl group, such as terephthaldehyde, to be fluorinated with a fluorinating reagent, for example $SF_4$, $MoF_6$, DAST or HF/Py at proper conditions. Despite a better yield of TFPX being achievable from such preparation, however, the price of the above-mentioned fluorinating reagent can be rather high. The equipments and preparation conditions can also be relatively unique and complex, and the leftover gases and liquid wastes are difficult to deal with, greatly raising the cost of preparing TFPX, thus making these methods unfavorable with respect to mass production.

Therefore, it is desirable to provide a safe, cost-effective and efficient synthesis method, such that a reduction in the cost of preparing TFPX can play a positive role in production expansion.

SUMMARY OF THE INVENTION

The present invention discloses a method for transferring TCPX ($\alpha$, $\alpha$, $\alpha'$, $\alpha'$-tetrachloro-p-xylene) into TFPX ($\alpha$, $\alpha$, $\alpha'$, $\alpha'$-tetrafluoro-p-xylene), which comprises the following steps: (a) providing a first reactant comprising TFPX; (b) mixing the first reactant with alkali metal fluorides, TCPX and phase transfer catalyst to form a mixture, wherein the alkali metal fluorides are KF, CsF, NaF, LiF or the combination thereof, the phase transfer catalysts (PTC) are a quaternary ammonium salt, quaternary phosphonium salt or the combination thereof; and (c) heating the mixture.

That is, the method of the present invention is to add a phase transfer catalyst in the fluorinating reaction between TCPX and alkali metal fluorides, by which the time required to react can be shortened, the temperature during the reaction can be decreased, and the overall output of TFPX can be increased. Also, since the reaction does not result in gelation or flocculation, the present method is valuable to be utilized in production expansion for industrial application.

In the method of the present invention, the first reactant can be solution that comprises TFPX. Therefore, the first reactant of the present invention preferably can be pure TFPX, or crude TFPX, that is, solutions containing 4F and 3F, 2F, or 1F. The following structures (4), (5), (6) and (7) present one of the states of 1F, 2F, 3F, and 4F respectively:

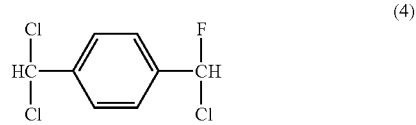

(4)

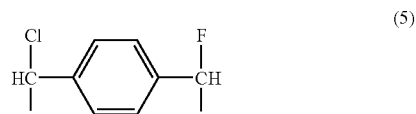

(5)

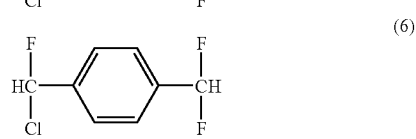

(6)

-continued

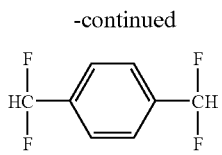

(7)

Additionally, the crude TFPX of the present invention can be obtained by any method in the art, preferably by which the crude product is obtained from a thermal reaction of TCPX, KF and a proper amount of phrase transfer catalyst. This crude product, under GC analysis, will be found comprising both TCPX, chlorine that has been partially replaced (3F, 2F and 1F), and chlorine that has been totally replaced (4F, TFPX).

In the method of the present invention, heating at a temperature above 100° C. in step (c) is preferably in the range of 130° C. to 250° C. In the method of the present invention, the heating time for reaction in step (c) is more than 3 hours, preferably from 3 to 36 hours. The method of the present invention further comprises an optional step (d) to clean the said product, preferably with water. Also, the method of the present invention further comprises an optional step (e) to extract TFPX from the said product, preferably with the use of ether to first extract the product followed by process of distillation in order to separate TFPX from the product. In the method of present invention, alkali metal fluorides and TCPX have a molar ratio of from 1 to 16, preferably from 4 to 8.

The phase transfer catalyst used in the method of the present invention can be quaternary ammonium salt, which has the structure (8) as follows:

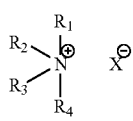

(8)

wherein the X is Cl, Br or I, and $R_1$, $R_2$, $R_3$ and $R_4$ are alkyl group, aryl group, or the combination thereof. This alkyl group is preferably $C_1$ to $C_8$ alkyl group, and the aryl group is preferably phenyl group or benzyl group. Hence, $R_1$, $R_2$, $R_3$ and $R_4$ of the quaternary ammonium salt in the present invention can preferably be the same alkyl group or different alkyl group. The quaternary ammonium salt can be $(CH_3)_4NCl$, $(C_4H_9)_4NBr$ or $(C_8H_{17})(CH_3)_3NBr$. Alternatively the quaternary ammonium salt can be $R_1$, $R_2$, $R_3$ sharing the same alkyl group while R4 is aryl group, such that the quaternary ammonium salt can be $(C_6H_5)(CH_3)_3NCl$, $PhCH_2N(CH_3)_3Br$ or $PhN(CH_3)_3Br$.

The phase transfer catalyst used in the method of the present invention can also be quaternary phosphonium salt, which has the structure (9) as follows:

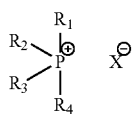

(9)

wherein the X is Cl, Br or I, and $R_1$, $R_2$, $R_3$ and $R_4$ are alkyl group, aryl group, or the combination thereof. This alkyl group is preferably $C_1$ to $C_8$ alkyl group, and the aryl group is preferably phenyl group or benzyl group. Hence, $R_1$, $R_2$, $R_3$ and $R_4$ of the quaternary phosphonium salt in the present invention can preferably be the same alkyl group, the same aryl group, a different alkyl group or a different aryl group. The quaternary phosphonium salt can be $(Ph)_4PBr$, $(C_4H_9)_4PBr$ or $(Ph)_3CPPh_3Cl$.

The phase transfer catalyst in the method of the present invention can be quaternary ammonium salt, quaternary phosphonium salt, or the combination thereof, preferably the combination of quaternary ammonium salt and quaternary phosphonium salt, in which the weight ratio of the quaternary ammonium salt to the quaternary phosphonium salt is in the range of from 0.5 to 5, preferably from 1 to 2.5.

DETAILED DESCRIPTION OF THE PREFERRED EMBODIMENT

EXAMPLE 1

Preparation of TFPX—Single PTC

The TFPX is prepared by mixing TCPX with dry KF at a 1:8 ratio respectively in terms of their molar ratio, heating to 240° C. and reacting for 36 hours. After distillation a product is obtained (the peak area % of the product that replaces 1~4 F obtained from GC analysis yields: 96.04% 4F and 3.86% 3F), and this product is referred to as the first reactant. Then 22.5 grams (0.093 mole) of TCPX and 45 grams (0.77 mole) of dry KF (molar ratio 1:8.3) are mixed and added into the reaction container, along with 1.2 grams (0.011 mole) of phase transfer catalyst (tetramethyl ammonium chloride) and 35 grams of the first reactant (TFPX). Using GC analysis, the peak area % of the mixture prior to the reaction consists 54.4% 4F (TFPX), 2.1% 3F and 43.5% TCPX. Then the mixture is stirred and heated to 190° C. to react for 21 hours; the GC analysis yields the peak area % of the product obtained which replaces 1~4 F: 79.2% 4F (TFPX), 0% 3F, 2.18% 2F, 1.68% 1F and 16.7% non-reacting TCPX. After 27 hours of reaction time, the peak area % of the product obtained which replaces 1~4 F yields 80.9% 4F (TFPX), 0% 3F, 2.31% 2F, 1.98% 1F and 14.73% non-reacting TCPX. After 44 hours of reaction time, the peak area % of the product obtained which replaces 1~4 F yields 82.2% 4F (TFPX), 0% 3F, 3.22% 2F, 2.09% 1F and 11.25% non-reacting TCPX.

EXAMPLE 2

6.08 grams (0.025 mole) of TCPX and 12 grams (0.206 mole) of dry KF (molar ratio 1:8.2) are mixed and added into the reaction container, along with 1.2 grams (0.011 moles) of phase transfer catalyst (tetraphenylphosphonium bromide) and 10.5 grams of the first reactant (TFPX). Using GC analysis, the peak area % of the mixture prior to the reaction consists 72.02% 4F (TFPX), 1.03% 2F and 26.93% TCPX. Then the mixture is stirred and heated to 190° C. to react for 6 hours, and the peak area % of the product obtained which replaces 1~4 F yields. 78.01% 4F (TFPX), 0.45% 3F, 12.03% 2F, 0.71% 1F and 8.78% non-reacting TCPX. The reaction is continued for a further 22 hours, whereafter the peak area % of the product obtained which replaces 1~4 F yields 91.21% 4F (TFPX), 0.62% 3F, 6.28% 2F, 0% 1F and 1.01% non-reacting TCPX.

EXAMPLE 3

Preparation of TFPX 6.03 grams (0.025 mole) of TCPX and 12.3 grams (0.21 mole) of dry KF (molar ratio 1:8.4) are mixed and added into the reaction container, along with the first reactant (crude TFPX) and phase transfer catalyst (0.3 gram of tetra n-butylammonium iodide). Before the reaction takes place, using GC analysis the peak area % of this mixture consists 73.17% 4F (TFPX), 0.38% 3F, 1.05 2F, 0.29% 1F and 24.53% TCPX. After mixture is stirred and heated to 170° C. to react for 5 hours, and the peak area % yields 79.78% 4F (TFPX), 0.32% 3F, 1.82% 2F, 1,08% 1F and 16.19% non-reacting TCPX. Reaction time is continued for a further 24 hours, whereafter the peak area % yields 83.53% 4F (TFPX), 0.33% 3F, 1.82% 2F, 1.57% 1F, 11.26% non-reacting TCPX, and approximately 1.5% other unidentified products.

EXAMPLE 4

Preparation of TFPX—Dual PTCs 20 grams (0.082 mole) of TCPX and 40 grams (0.69 mole) of dry KF (molar ratio 1:8.4) are mixed along with 40 grams of the first reactant (TFPX) and dual phase transfer catalysts (2 grams (0.018 mole) of tetramethyl ammonium chloride and 2 grams (0.004 mole) of tetraphenylphosphonium bromide) and all added into the reaction container to form a mixture. Then the mixture is stirred and heated up until 190° C. to react for 5 hours; using GC analysis, the peak area % of the product obtained which replaces 1~4 F yields 94.63% 4F (TFPX), 0% 3F, 5.37% 2F, 0% 1F and 0% TCPX. Followed by cleansing with water, the mixture is extracted with ether, and 51 grams of pure TFPX (b.p 85° C./30 mm) can be obtained through distillation, at an output yield of 74.8%. The final product analysis is the following:

GC Analysis (varian chrompack capillary column CP7735): single peak

| $H^1$NMR Analysis: | $\delta_{TMS}$ | 7.52 ppm(singlet 4H) |
|---|---|---|
|  | $\delta_{TMS}$ | 6.68 ppm(triplet 2H) |
| $F^{19}$NMR Analysis: | $\delta_{CFCl3}$ | −111.8 ppm(doublet $J_{HF}$ = 57 cps) |

Elemental Analysis: $C_8H_6F_4$

|  | C (%) | H (%) |
|---|---|---|
| Theoretical value | 53.93 | 3.37 |
| Actual value | 54.70 | 3.30 |

EXAMPLE 5

Preparation of TFPX—Decrease in Use of PTC 20.5 grams (0.084 mole) of TCPX and 42 grams (0.72 mole) of dry KF (molar ratio 1:8.5) are mixed along with 42 grams of the first reactant (TFPX) and dual phase transfer catalysts with a lower amount than that in Example 4 (2 grams (0.018 mole) of tetramethyl ammonium chloride and 1 grams (0.002 mole) of tetraphenylphosphonium bromide) and all added into the reaction container to form a mixture. The mixture is then stirred and heated to 190° C. to react for 5 hours; using GC analysis, the peak area % of the product obtained which replaces 1~4 F yields 88.89% 4F (TFPX), 0% 3F, 8.02% 2F, 0% 1F, 0.99% TCPX and 2.1% unidentified products. For 8 hours of reaction time, the peak area % of the product obtained which replaces 1~4 F yields 90.74% 4F (TFPX), 1.21% 3F, 3.92% 2F, 0% IF, 0% TCPX and 4.1% unidentified products, showing that TCPX has been completely transferred.

Having it cleansed with water and extracted with ether, 52 grams of pure TFPX can be obtained through distillation, at an output yield of 66.4%.

EXAMPLE 6

Preparation of TFPX—Decrease in Use of PTC 6.0 grams (0.025 mole) of TCPX and 12 grams (0.206 mole) of dry KF (molar ratio 1:8) are mixed in the reaction container, and 10 grams of the first reactant (crude TFPX) and dual phase transfer catalysts (0.3 gram of tetra n-butylammonium iodide and 0.3 gram of tetra n-butylphosphonium chloride) are also added in. Prior to reaction, GC analysis consists the peak area % as 72.11% 4F (TFPX), 0.36% 3F, 1.03 2F, 0.25% 1F and 26.23% TCPX. After mixture is stirred and heated to 170° C. to react for 5 hours, and the peak area % yields: 86.84% 4F (TFPX), 0.86% 3F, 7.32% 2F, 0.52% 1F and 4.44% TCPX. The reaction is continued for a further 24 hours, whereafter the peak area % yields 95.04% 4F (TFPX), 2.84% 3F, 0.39% 2F, 0% 1F, 0.16% non-reacting TCPX, and approximately 1.5% unidentified products.

EXAMPLE 7

Preparation of TFPX—Decrease in Use of Fluorinating Reagent—KF 25 grams (0.102 mole) of TCPX and 38 grams (0.656 mole) of dry KF (molar ratio 1:6.4) are mixed along with 30 grams of TFPX (first reactant) and dual phase transfer catalysts (2.5 grams of tetramethyl ammonium chloride and 1.25 grams of tetraphenylphosphonium bromide) and all added into the reaction container to form a mixture. Then the mixture is stirred and heated to 170° C. to react for 5 hours; using GC analysis, the peak area % of the product obtained which replaces 1~4 F yields 71.33% 4F (TFPX), 0.64% 3F, 17.77% 2F, 0.71% 1F and 9.54% non-reacting TCPX. The reaction is continued for a further 21 hours, whereafter the peak area % of the product obtained which replaces 1~4 F yields 91.88% 4F (TFPX), 0.50% 3F, 7.61% 2F, 0% non-reacting TCPX, showing that nearly all the TCPX has been completely transferred.

COMPARATIVE EXAMPLE 1

Preparation of TFPX—without PTC 50 grams (0.205 mole) of TCPX and 100 grams (0.1.722 mole) of dry KF (molar ratio 1:8.4) are mixed along with 50 grams of TFPX (first reactant). Then the mixture is stirred and heated up until 170° C. to react for 22 hours; using GC analysis, the peak area % of the product obtained which replaces 1~4 F yields 1.29% 3F and 1.81% 2F without evident increase in 4F (TFPX). Accordingly, given the conditions of the reaction (temperature and time), TFPX (4F) cannot be obtained without any phase transfer catalyst in the chlorine displacement reaction.

COMPARATIVE EXAMPLE 2

Preparation of TFPX by Solid-State Reaction—without PTC and First Reactant

TFPX is prepared by mixing TCPX and dry KF at a 1:8 ratio in terms of their molar ratio, then heating to 240° C. and reacting for 36 hours. Once the reaction reaches an end, using GC analysis the peak area % of the product which replaces 1~4F yields 20% 4F (TFPX), 3% 3F, 40% 2F, 32% 1F and 5% TCPX.

As mentioned above, it is known that the method for preparing TFPX in the prior art (i.e. comparative example 2) was to have TCPX directly reacted with alkali metal fluorides, enforcing fluorine atoms substitute for four chlorine atoms. Yet the laboratory results in the comparative example 2 clearly show the product of which using GC analysis merely yields 20% TFPX (4F) that is left with 75% incompletely-transferred fluorine substitutions (3F, 2F and 1F) and 5% non-reacting TCPX. That is, the conventional method in the art for preparing TFPX possesses relatively low output yield. Besides, the issue of gelation hinders the application from production expansion and even further application on preparing parylene polymer. By comparison, the method of the present invention utilizes the employment of phase transfer catalyst to increase the fluorination process in transferring TCPX to TFPX in a great scale, allowing the output yield to be increased. The reaction performs especially well in terms of the fluorine substitution by adding dual phase transfer catalysts, for instance, the GC analysis of the product obtained in Example 4 shows a clear increase in the yield of output as the organic compound having chlorine atoms—TCPX can be mostly transferred to TFPX (4F) at 94%, only left with 5% partial fluorine substitutes 2F. Moreover, the reaction can be compressed down to 5 hours with the use of dual phase transfer catalysts. The present invention not only exhibits non-obviousness with respect to its transferring ratio from TCPX to TFPX, the reaction temperature is also reduced while reaction time is shortened significantly. Furthermore, since the first reactant of the present invention can be operated as a solvent, with which the reaction will result in no gelation, the present invention is applicable to production expansion such that it possesses advanced utility properties for the benefit of the relevant industries.

Although the present invention has been explained in relation to its preferred embodiment, it is to be understood that many other possible modifications and variations can be made without departing from the scope of the invention as hereinafter claimed.

What is claimed is:

1. A method for transferring TCPX (α, α, α', α'-tetrachloro-p-xylene) into TFPX (α, α, α', α'-tetrafluoro-p-xylene), which comprises the following steps:
   (a) providing a first reactant comprising TFPX;
   (b) mixing said first reactant with alkali metal fluorides, TCPX and phase transfer catalyst(s) to form a mixture, wherein the alkali metal fluorides is KF, CsF, NaF, LiF or the combination thereof; the phase transfer catalyst(s) is quaternary ammonium salt, quaternary phosphonium salt or the combination thereof; and
   (c) heating said mixture to obtain a product.

2. The method of claim 1, wherein said first reactant is pure TFPX or crude TFPX.

3. The method of claim 1, wherein the heating temperature in step (c) is in the range of 130° C. to 250° C.

4. The method of claim 1, wherein the heating time in step (c) is more than three hours.

5. The method of claim 1, wherein further comprising a step (d) cleansing said product.

6. The method of claim 1, wherein further comprising a step (e) extracting TFPX from said product.

7. The method of claim 1, wherein the molar ratio of said alkali metal fluorides to said TCPX is 1 to 16.

8. The method of claim 1, wherein said quaternary ammonium salt has the structure:

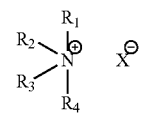

(8)

wherein X is Cl, Br or I, and $R_1$, $R_2$, $R_3$ and $R_4$ are alkyl group, aryl group, or the combination thereof.

9. The method of claim 8, wherein said alkyl group is $C_1$ to $C_8$ alkyl group, and said aryl group is phenyl group or benzyl group.

10. The method of claim 8, wherein said quaternary ammonium salt is tetramethyl ammonium chloride or tetra n-butylammonium iodide.

11. The method of claim 1, wherein said quaternary phosphonium salt has the structure:

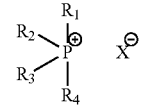

(9)

wherein X is Cl, Br or I, and $R_1$, $R_2$, $R_3$ and $R_4$ are alkyl group, aryl group, or the combination thereof.

12. The method of claim 11, wherein said alkyl group is $C_1$ to $C_8$ alkyl group, and said aryl group is phenyl group or benzyl group.

13. The method of claim 11, wherein said quaternary phosphonium salt is tetraphenylphosphonium bromide or tetra n-butylphosphonium chloride.

14. The method of claim 1, wherein said phase transfer catalyst is a mixture of said quaternary ammonium salt and said quaternary phosphonium salt, and the weight ratio of said quaternary ammonium salt to said quaternary phosphonium salt is in the range of from 0.5 to 5.

15. The method of claim 1, wherein the weight ratio of said phase transfer catalyst to said TCPX is in the range of from 0.01 to 0.20.

* * * * *